(12) United States Patent
Sarna

(10) Patent No.: US 9,173,571 B2
(45) Date of Patent: Nov. 3, 2015

(54) SYSTEMS AND METHODS FOR MAINTAINING A NARROW BODY LUMEN

(75) Inventor: Surbhi Sarna, San Francisco, CA (US)

(73) Assignee: nVision Medical Corporation, San Francisco, CA (US)

( * ) Notice: Subject to any disclaimer, the term of this patent is extended or adjusted under 35 U.S.C. 154(b) by 218 days.

(21) Appl. No.: 13/979,691

(22) PCT Filed: Jan. 25, 2012

(86) PCT No.: PCT/US2012/022619
§ 371 (c)(1),
(2), (4) Date: Jul. 15, 2013

(87) PCT Pub. No.: WO2012/103266
PCT Pub. Date: Aug. 2, 2012

(65) Prior Publication Data
US 2013/0296686 A1  Nov. 7, 2013

Related U.S. Application Data

(60) Provisional application No. 61/435,945, filed on Jan. 25, 2011.

(51) Int. Cl.
| | | |
|---|---|---|
| A61B 5/05 | (2006.01) |
| A61B 5/00 | (2006.01) |
| A61B 1/00 | (2006.01) |
| A61B 1/05 | (2006.01) |
| A61B 1/012 | (2006.01) |
| A61B 1/303 | (2006.01) |

(52) U.S. Cl.
CPC ............ *A61B 5/0082* (2013.01); *A61B 1/00147* (2013.01); *A61B 1/05* (2013.01); *A61B 1/012* (2013.01); *A61B 1/303* (2013.01)

(58) Field of Classification Search
CPC ............... A61B 17/22; A61B 1/00156; A61B 1/00082; A61B 1/005; A61B 1/041; A61B 1/008; A61N 5/1007; A61N 5/1002; A61M 25/1002; A61M 25/0028
See application file for complete search history.

(56) References Cited

U.S. PATENT DOCUMENTS

| | | | |
|---|---|---|---|
| 5,456,680 A | 10/1995 | Taylor et al. |
| 5,662,587 A * | 9/1997 | Grundfest et al. | ............ 600/114 |
| 6,178,346 B1 | 1/2001 | Amundson et al. |
| 6,503,185 B1 | 1/2003 | Waksman et al. |
| 2002/0120178 A1* | 8/2002 | Tartaglia et al. | ............ 600/114 |
| 2007/0244359 A1 | 10/2007 | Cabiri et al. |

* cited by examiner

*Primary Examiner* — Joel Lamprecht
(74) *Attorney, Agent, or Firm* — Alan W. Cannon; Law Office of Alan W. Cannon

(57) ABSTRACT

Devices and processes for maintaining a narrow body lumen are described. One embodiment of the inventive device includes: (i) a hydraulic propulsion mechanism for propelling an imaging portion or a therapeutic portion through the narrow body lumen; and (ii) a retrieval mechanism for retrieving the imaging portion or the therapeutic portion from the narrow body lumen.

24 Claims, 10 Drawing Sheets

SYSTEMS AND METHODS FOR MAINTAINING A NARROW BODY LUMEN

RELATED APPLICATION

This application is filed under 35 USC §371 as a national stage of PCT/US2012/022619, filed 25 Jan. 2012, which claims priority from U.S. Provisional Application having Ser. No. 61/435,945, which was filed on Jan. 25, 2011, both of which are hereby incorporated herein by reference thereto for all purposes and which we claim priority to.

FIELD OF THE INVENTION

The present invention relates generally to maintenance of a narrow body lumen. More particularly, the present invention relates to systems or methods for diagnostic imaging or therapeutic treatment to effectively maintain the narrow body lumen.

BACKGROUND OF THE INVENTION

For a variety of reasons, occlusions often develop in narrow body lumens (i.e., the channel of a tubular-shaped anatomical structure, such as the fallopian tubes, intestines, and coronary arteries) and have medically-relevant consequences on the body. Conventional techniques employed to maintain the health of fallopian tubes, as an example of a narrow body lumen, are described below.

Fallopian tubes are vessel-like, non-fluid filled structures that extend from the uterus to the ovaries. On average, fallopian tubes measure between eight and ten centimeters in length. The inner diameter of the tube varies significantly depending on the segment of the tube, with a minimum inner diameter of approximately one millimeter and a maximum of six millimeters. Along the length of the lumen of the fallopian tube millions of microscopic hair-like cilia pulsate in wave-like motions at the rate of hundreds of times per second. This motion assists the egg, delivered from the ovaries during ovulation, in passing through the tube to the uterine cavity. Cells located in the tube's inner lining (endothelium) supply the egg with vital nourishment and provide lubrication along the path. It is within the fallopian tube that the sperm first contacts the egg. If the egg is not fertilized within twenty-four to thirty-six hours of reaching the fallopian tube, the egg deteriorates and is removed from the tube by the body's immune system.

Disease of fallopian tube often presents as occlusion or thickening of the fallopian tube wall and can be caused by infection as well as scarring. In particular, pelvic inflammatory disease (PID), urinary tract infections (UTI) as well as sexually transmitted infections (STI) may cause severe inflammation that in turn blocks the tube. Endometriosis may also cause occlusion when the uterine lining grows into the fallopian tube. An appendectomy or other abdominal surgery may further similarly lead to occluded fallopian tubes. Regardless of the manner in which it is formed, an occlusion can lead to a hydrosalpinx, where the tube increases in diameter because it is filled with fluid. The presence of fluid prevents both the egg and sperm from traveling through the fallopian tube, preventing fertilization. It is believed that hydrosalpinx can reduce the success rate of in-vitro fertilization by up to 8%.

In the US alone, there are at least seven million cases of infertility annually and an estimated 25-40% of these cases are caused by fallopian tube occlusion or disease. Hysterosalpingogram (HSG), a procedure most commonly utilized to diagnose fallopian tube disease, requires a radiologist to inject dye into the uterus under x-ray guidance. The dye enters the fallopian tube through the ostia (openings) located in the uterus. If a woman's fallopian tubes are patent (open), dye will flow into the peritoneal cavity. In order to visualize the fluid path, a series of timed x-rays are taken.

Unfortunately, this procedure suffers from several drawbacks. By way of example, HSG suffers from a high false negative rate of 30% and a high false positive rate of 40% due to tubal spasms or shadow (noise) in the x-rays. This often necessitates further procedures. This high rate of inaccuracy is also partly due to the fact that radiologists are not as intimate with the tortuosity and topography of the fallopian tube as gynecologist or reproductive endocrinologist.

As another example of a drawback, HSG is not conducted in-office by a gynecologist or reproductive endocrinologist, the primary caretaker of the patient, as it necessitates a substantial investment in x-ray capital equipment mostly found in hospitals. The patient typically first visits a gynecologist, who conducts a series of blood tests and determines whether HSG is necessary. If it is deemed necessary, then the patient schedules an appointment with the radiologist to have the HSG procedure administered. At the conclusion of the first procedure, the patient returns either to the gynecologist or reproductive endocrinologist to discuss the results. Because of the high inaccuracy rate associated with the HSG, the patient often returns to the radiologist for a second procedure, creating additional unnecessary costs for both the patient and hospital.

As yet another example, patients often complain of pain and some are allergic to the dye used during the procedure. Furthermore, HSG must be conducted before day 12 of a woman's menstrual cycle because the dye may harm a potential full term pregnancy, which limits options for both doctor and patient and further extends the waiting period for a full infertility diagnosis, which is emotionally taxing to the patient and family.

To overcome these drawbacks, different direct visualization techniques have been attempted. FIG. 1 shows an endoscope, which uses conventional optical fiber imaging technology, as an exemplar attempt to achieve direct visualization of the fallopian tubes. In this figure, a female reproductive anatomy 10 undergoing imaging includes fallopian tubes 12, ovaries 14, uterus 16, uterine cavity 22, cervix 28 and fimbria 30. An imaging catheter shaft 20 is introduced into a fallopian tube, which has a consistency of a wet paper towel. Catheter shaft 20 passes through fallopian tube ostia in the uterus 18, beyond which point the fallopian tube 12 is narrow and tortuous.

Unfortunately, the wet-paper-towel consistency does not provide adequate tactile feedback to a physician, who navigates catheter 20 through fallopian tube 12. As a result, during the imaging procedure, the physician is not aware of the undue pressure exerted against the fallopian tube, leading to perforation 24. To this end, FIG. 1 shows a portion of catheter 26 protruding out of perforation 24 in fallopian tubes 12. Perforation of the fallopian tube may prevent eggs from the ovaries 14 of the patient from reaching the uterus 16 for fertilization, making perforation an unacceptable clinical adverse event in a patient who is actively attempting to conceive. In addition to running the risk of perforating the fallopian tubes, the imaging procedure described above involves several steps and is therefore viewed by physicians as convoluted and difficult to perform correctly. Furthermore, the wet paper towel consistency of the fallopian tubes prevents the attempted imaging procedure from obtaining a clear, focused image. Specifically, during imaging, the wet paper towel consistency causes the fallopian tubes' walls to "fold" over the endoscope's tip, making it difficult to maintain a sufficient distance between the endoscope's tip and the walls of the fallopian tubes to focus and take a clear picture.

Therefore, what is needed is a novel diagnostic and therapeutic system and method which allows for effective maintenance of a narrow body lumen, without suffering from the drawbacks encountered by the current and attempted systems and methods described above.

SUMMARY OF THE INVENTION

In view of the foregoing, in one aspect, the present invention provides a device for maintaining a narrow body lumen (e.g., the channel of a tubular-shaped anatomical structure, such as the fallopian tubes, intestines, and coronary arteries). The device includes: (i) a hydraulic propulsion mechanism for propelling an imaging portion or a therapeutic portion through the narrow body lumen; and (ii) a retrieval mechanism for retrieving the imaging portion or the therapeutic portion from the narrow body lumen.

In one embodiment of the present invention, the device further includes a handle portion, which receives one or more luers, one of which is designed to provide hydraulic pressure to hydraulically propel the imaging portion or the therapeutic portion through the narrow body lumen. The luer is preferably designed to receive a hydraulic propellant from a reservoir containing the hydraulic propellant.

The device may further include a wire luer, which is received by the handle portion and is designed to provide a wire for conveying electrical power and signals to facilitate an imaging function carried out by the imaging portion.

The device may further still include a seal-creating lure, which is received by the handle portion and is designed to create a seal to facilitate imaging or therapeutic treatment. In certain embodiments of the present invention, an inflatable object is used for creating a seal to facilitate imaging or therapeutic treatment. In these embodiments, the seal-creating lure may also be referred to as an inflation luer as it facilitates inflation of the inflatable body.

In another aspect, the present invention provides a narrow body lumen diagnostic device. The device includes: (i) a guide wire capable of providing light or sensing an image and for guiding a catheter to a target location, the guide wires including illuminating fibers or imaging fibers; and (ii) a catheter including imaging fibers if the guide wire includes illuminating fibers or the catheter including illuminating fibers if the guide wire includes imaging fibers.

In yet another aspect, the present invention provides a fallopian tube diagnostic device. The device includes: (i) a sensing lumen for providing a catheter including a sensing portion and an inflatable portion, and the sensing portion capable of sensing information about the fallopian tube; (ii) a solution lumen for providing a solution which facilitates sensing carried out by the sensing portion; and (iii) wherein, in an operational state of the fallopian tube diagnostic device, the inflatable portion inflates to create a space around the sensing portion such that in presence of the solution, the sensing portion senses information regarding the fallopian tube. In certain preferred embodiments of the present invention, the device includes a therapeutic lumen to provide therapy to a localized region in the fallopian tube.

In yet another aspect, the present invention provides a process of maintaining a narrow body lumen. The process includes: (i) creating a seal inside or outside the narrow body lumen such that in presence of a hydraulic propellant, the narrow body lumen is pressurized to allow diagnostic imaging of the narrow body lumen using an imaging portion of an imaging device; (ii) hydraulically propelling, using the hydraulic propellant, the imaging portion through the narrow body lumen; (iii) imaging the narrow body lumen; and (iv) retrieving the imaging portion from the narrow body lumen.

In a preferred embodiment of the present invention, the above-described process includes: (i) establishing a channel from outside the narrow body lumen to a proximal region of the narrow body lumen or a region that is proximate to the narrow body lumen; (ii) placing the imaging portion through the channel; and (iii) wherein the placing is carried out before the creating.

In yet another aspect, the present invention provides a process for maintaining a narrow body lumen. The process includes: (i) sealing the narrow body lumen to allow therapeutic treatment of the narrow body lumen using a therapeutic device; (ii) hydraulically propelling the therapeutic device through the narrow body lumen; (iii) treating the narrow body lumen; and (iv) retrieving the therapeutic device from the narrow body lumen.

The process may further include: (i) defining a channel from outside the narrow body lumen to a proximal region of the narrow body lumen or a region that is proximate to the narrow body lumen; (ii) placing the therapeutic device through the channel; and (iii) wherein the placing is carried out before the sealing.

In yet another aspect, the present invention provides a process of maintaining a fallopian tube. The process includes: (i) steering a guide wire through a channel to a target location within a fallopian tube and the guide wire capable of providing light or imaging; (ii) placing over the guidewire a catheter for providing light or imaging; (iii) imaging or illuminating the fallopian tube using the guide wire and the catheter; and (iv) retrieving the catheter from the fallopian tube.

The process may further includes: (i) removing the guidewire from a guidewire lumen; and (ii) introducing a therapy or a saline flush through the guidewire lumen.

The construction and method of operation of the invention, however, together with additional objects and advantages thereof, will be best understood from the following descriptions of specific embodiments when read in connection with the accompanying figures.

BRIEF DESCRIPTION OF THE DRAWINGS

FIG. 2A shows a magnified view of a distal tip of a shaft portion of the diagnostic device shown in FIG. 2.

FIG. 2B shows a side-sectional view of a distal tip of a shaft portion of a therapeutic device, according to one embodiment of the present invention.

DETAILED DESCRIPTION OF THE PREFERRED EMBODIMENTS

Figure 1:
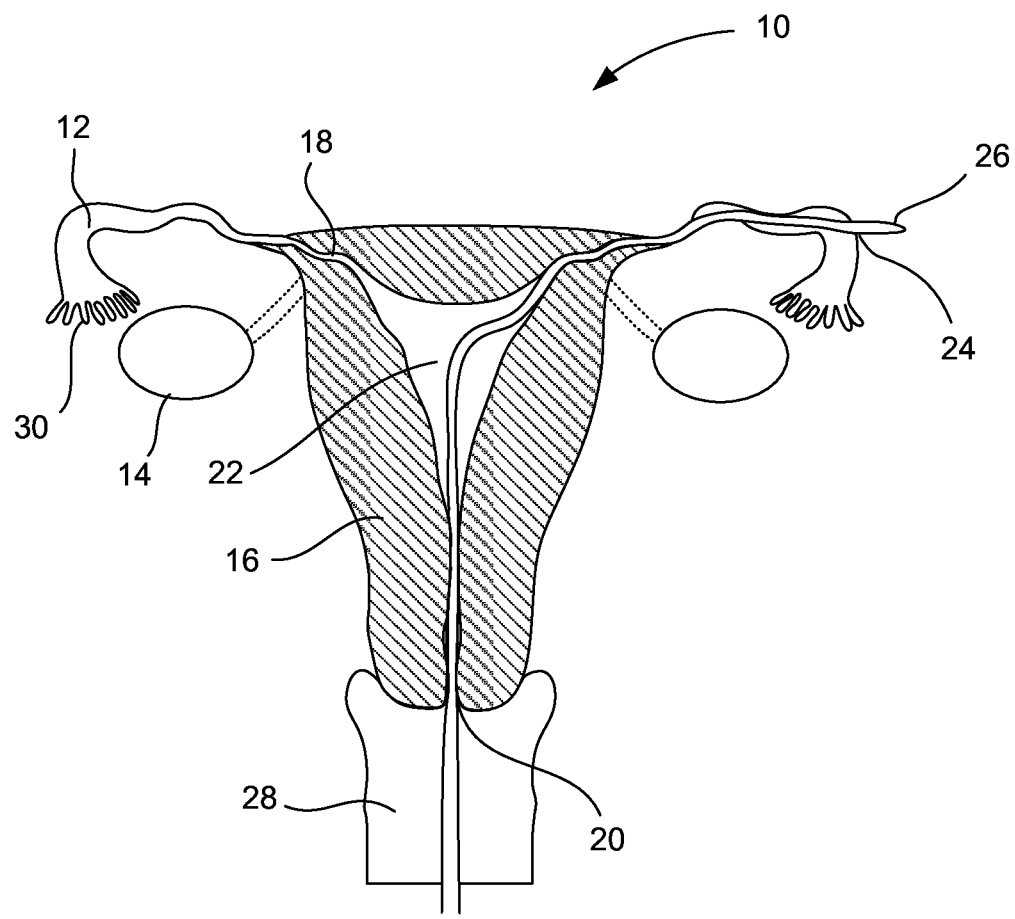
FIG. 1 shows an endoscope being navigated through the fallopian tubes and major organs of a female reproductive system.

In the following description, numerous specific details are set forth in order to provide a thorough understanding of the present invention. It will be apparent, however, to one skilled in the art that the present invention may be practiced without limitation to some or all of these specific details. In other instances, well-known process steps have not been described in detail in order to not unnecessarily obscure the invention.

In certain embodiments, the present invention provides novel systems and methods for accurate real time-visualization, which dynamically diagnose malfunction of the fallopian tubes. In preferred embodiments of the present invention, a single-use, disposable product and its associated procedure overcomes the many drawbacks encountered with current and attempted diagnostic approaches. The present inventions' more accurate, dynamic procedure may be conducted in an office of a gynecologist or a reproductive endocrinologist, who is typically the first and main point of contact for an infertility patient, understands the anatomy in question, and is better trained to dynamically change or repeat steps in the procedure if further clarification is needed. As a result, the number of office visits and costs to both the patient and hospital are significantly reduced, and at the same time, convenience to the parties involved is significantly increased. Furthermore, the high false positive rate of 20% to 40% encountered by the conventional diagnostic systems and procedures is also reduced by the present inventions' ability to directly visualize the fallopian tubes.

Preferred embodiments of the present invention recognize that to carry out certain initial steps of the inventive procedures, conventional diagnostic procedures may be relied upon to an extent. By way of example, certain inventive procedures require visualization of the openings (ostia) of the fallopian tubes in the uterus so that the tubes may be accessed. Those skilled in the art will recognize that although conventional hysteroscopes were primarily used to evaluate and maintain the health of a uterus, due to recent advancements in less invasive sterilization procedures such as Essure and Adiana (during which the tube is purposely occluded), a large numbers (e.g., up to 7,500 for the Essure alone) of gynecologists and reproductive endocrinologists have adopted the hysteroscopes to visualize, and trans-vaginally access, the fallopian tube. The present invention proposes to use the hysteroscope's working channel, in certain embodiment of the present invention. Once gynecologists or reproductive endocrinologists own or lease a hysteroscope (and the associated capital equipment), they are free to use the inventive procedures of the present invention using the working channel of the hysteroscope because they are unlimited in terms of which procedures they may conduct using their hysteroscope. It is noteworthy that the working channel of any catheter, which can visualize and gain access to the ostia of the fallopian tubes within the uterus, may be utilized by the present invention.

In preferred embodiments of the present invention, navigating a substantially transparent capsule, which houses a camera portion through the tortuous and narrow fallopian tubes by using a hydraulic propulsion method, has several advantages over navigating a purely catheter-based product through the fallopian tubes. By way of example, hydraulic propulsion overcomes the clinical adverse event of perforation, a drawback of previous direct visualization technologies. In other preferred embodiments of the present invention, hydraulic propulsion avoids perforation as the device does not depend on the tactile feedback of the fallopian tube. Instead, the hydraulic propellant carries the camera portion through the natural path of the fallopian tube.

Figure 2:
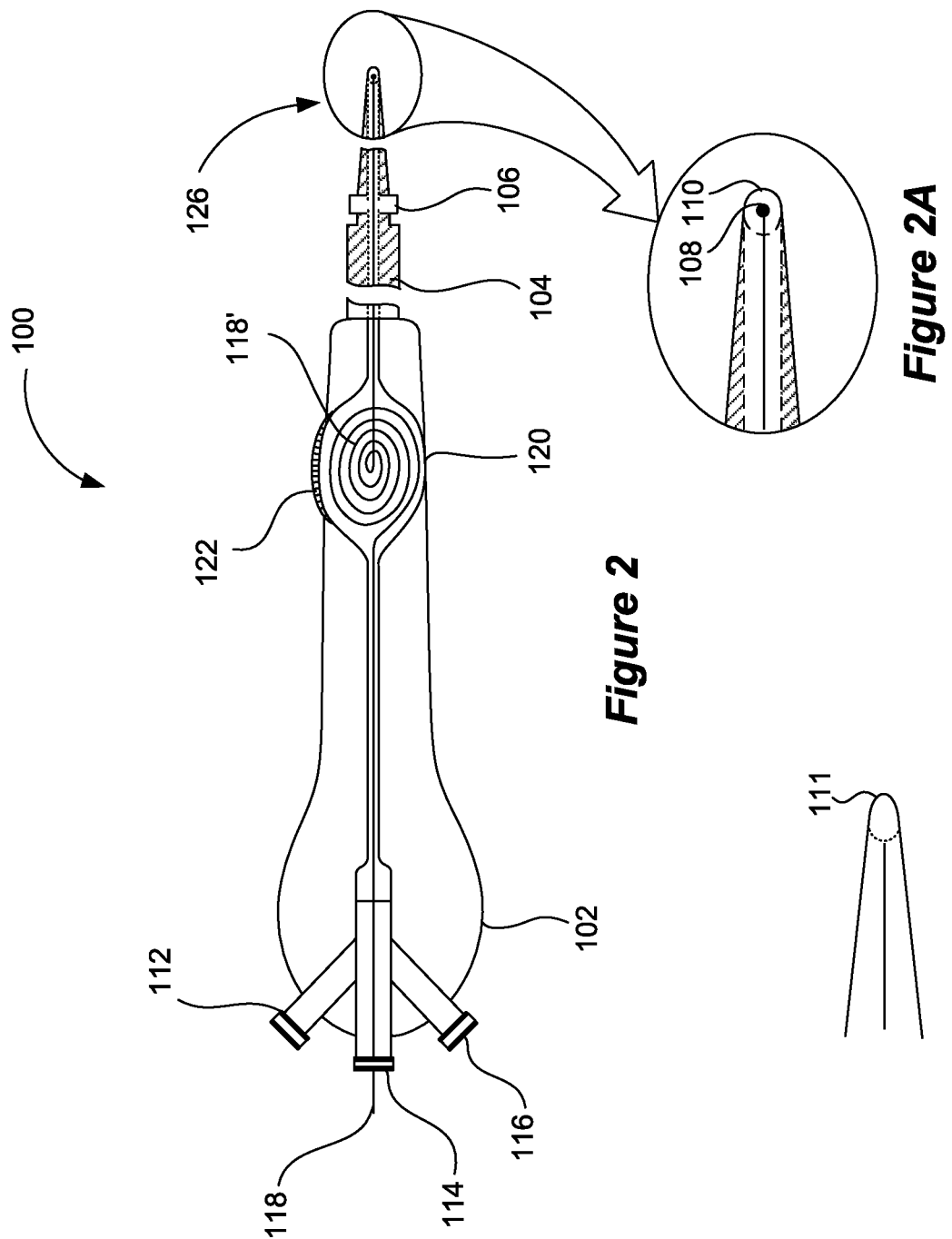
FIG. 2 shows a side-sectional view of a diagnostic device, according to one embodiment of the present invention, in a non-operational state.

In accordance with one embodiment, the present invention provides a hydraulic propulsion device that uses a working channel of a hysteroscope to access the ostia of the fallopian tubes. To this end, FIG. 2 shows a hydraulic propulsion device 100 having a handle portion 102, a shaft portion 104, and a seal-creating portion 106. As shown in FIG. 2A, which shows a magnified view of a tip of hydraulic propulsion device 100, device 100 includes an imaging subassembly 108 and a capsule 110.

Referring back to FIG. 2, handle portion 102 may come equipped with a hydraulic pressure port 112, which is designed to receive a hydraulic propellant (e.g., a saline solution) from a hydraulic propellant reservoir, such as a syringe. Hydraulic pressure port 112 is preferably communicatively coupled to a hydraulic pressure lumen (not shown to simplify illustration) which extends from handle portion 102 through shaft portion 104 to a location near imaging subassembly 108.

Similarly, an electrical wire 118 runs from handle portion 102 through shaft portion 104 and is communicatively coupled to imaging subassembly 108. Electrical wire 118 enters a handle portion at an electrical access port 114, which connects to a wire lumen. Electrical wire 118 is placed inside the wire lumen, which also extends from handle portion 102 through shaft portion 104 to a location near image subassembly 108.

A seal-creating port 116 of FIG. 2 facilitates a step of creating a seal at an ostia 18 of the fallopian tubes 12 or inside the proximal region of the fallopian tubes. These anatomies are shown in FIG. 1. Specifically, seal-creating port 116 of FIG. 2 is communicatively coupled to a seal-creating lumen (not shown to simplify illustration), which transports the necessary materials for creating a seal to seal—creating portion 106. In preferred embodiments, seal-creating portion 106 of the present invention is an inflatable body and the seal-creating port 116 is an inflatable port. In these embodiments, the seal-creating lumen is designed to convey air or other gas that inflates the inflatable body and the seal-creating lumen may be referred to as the "inflation lumen."

Figure 3:
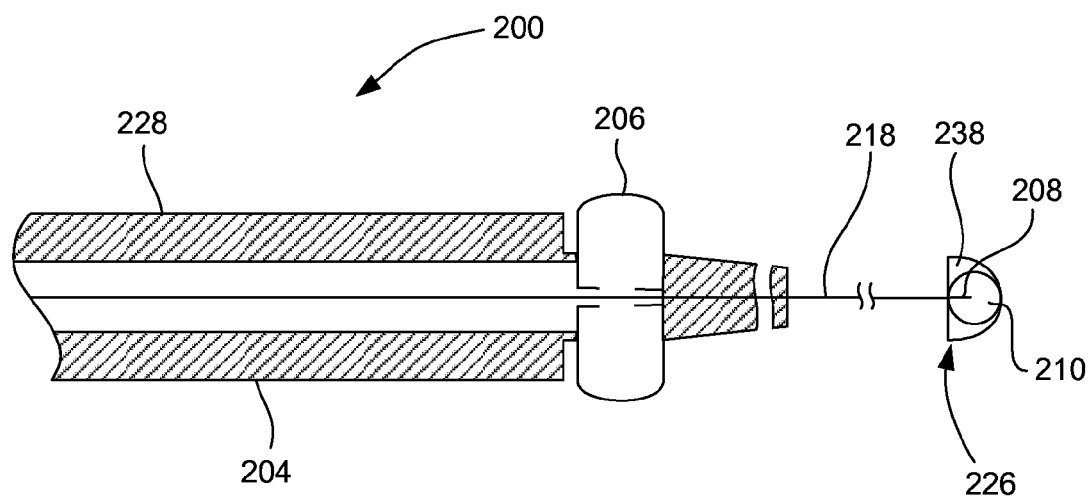
FIG. 3 shows a side-sectional view of a shaft portion, according to another embodiment of the present invention, in an operational state of the diagnostic device of FIG. 2.

In addition to one or more of the ports and lumens described above, handle portion 102 preferably includes a housing 120 for holding in place coiled wire 118', and a wire retrieval mechanism 122 to retrieve a hydraulically propelled wire in an operational state of device 100 (which is shown as device 200 in FIG. 3). Not all features of housing 120 are shown to simplify illustration and those skilled in the art will recognize that wire retrieval mechanism 122, in a preferred embodiment of the present invention, is akin to a fishing rod, which has a reel mechanism for casting and retrieving a fishing line. In this embodiment, retrieval mechanism 122 includes flexible wire 118 and a reel capable of reeling back the flexible wire from a propelled state. During an operational state of device 100, when the reel is activated, imaging subassembly 108 is retrieved back from a propelled state, preferably into handle portion 102.

In a more preferred embodiment of the present invention, retrieval mechanism 122 includes an electronically activated reel, which electronically activates retrieval of the reel from the propelled state of the reel. In this embodiment, inventive devices include a pressure sensor for conveying a pressure measurement to the electrically activating reel mechanism such that if the pressure exceeds a predetermined value of pressure, then the electrically activating reel mechanism ceases to retrieve imaging subassembly 108. The pressure sensor may be designed to sense the pressure exerted on imaging subassembly 108, as it is retrieved from the narrow body lumen.

As part of shaft portion 104, seal-creating portion 106 (e.g., inflatable body) is located outside and distal to handle portion 102. In this configuration and when device 100 is in an operational state, imaging portion 108 forms a perfect seal with an inner diameter of the hydraulic propellant lumen, as shown in FIG. 2A. As is explained later in connection with FIG. 3, this seal allows for hydraulic propulsion of imaging portion 108. In other preferred embodiments of the present invention, device 100 includes a locking mechanism, which locks imaging portion 108 within the inner diameter of the hydraulic propellant lumen until a requisite pressure is achieved to enable hydraulic propulsion.

Image subassembly 108 preferably includes an image sensor and a light source. The image sensor can be any object that is capable of sensing an image. In a preferred embodiment of the present invention, the image sensor includes at least one member selected from a group consisting of a charge coupled device (CCD), a complementary metal oxide semiconductor (CMOS) and an optical fiber. The light source includes a fiber optics light source or a light emitting diode ("LED").

In certain embodiments of the present invention, an inflatable object contains the image sensor and the lighting source such that when the inflatable body is inflated, the imaging sensor is positioned near or at an approximate focal length away from the narrow body lumen to allow focused imaging of the narrow body lumen. In this embodiment, the focal length is associated with the imaging sensor. If the image sensor is a camera, then the focal length referred to herein is that of the camera.

As shown clearly in FIG. 2A, capsule 110 protects a portion of imaging subassembly 108. In one embodiment of the present invention, capsule 110 is coated with a lubricant to facilitate hydraulic propulsion or retrieval of the capsule through the narrow body lumen. Capsule 110 preferably encapsulates a wireless transmitter for wirelessly transmitting images captured by an imaging sensor of imaging subassembly 108. In certain preferred embodiments, capsule 110 of the present invention encapsulates a pressure sensor, which senses an amount of pressure being applied against the narrow body lumen to determine presence of blockages within the narrow body lumen.

Capsule 110 is substantially round and therefore avoids causing tissue trauma, which is a drawback of previously attempted direct visualization devices. Furthermore, capsule 110 has centered within it imaging portion 108. The positioning of imaging portion 108 within capsule 110 overcomes the drawback of the fallopian tube hanging over the distal end of the catheter, preventing an inadequate focal length and therefore unclear picture from being taken.

In one embodiment of the present invention, the capsule is designed for encapsulating an inflatable body to enhance buoyancy of a portion of imaging subassembly 108 that is deployed inside the narrow body lumen during hydraulic propulsion. In such embodiments, capsule 110 of the present invention facilitates hydraulic propulsion of the propelled imaging portion as the inflatable body makes the capsule more easier carried by the hydraulic propellant.

In certain embodiments of the present invention, capsule 110 encapsulates a microgenerator, which uses the hydraulic propellant to provide power for the light source or the imaging sensor. In this embodiment, the microgenerator of the present invention converts hydraulic energy into electrical energy. This electrical energy is then used to power imaging portion 108 of the device. In other embodiments of the present invention, capsule 110 encapsulates optical fibers, which facilitate imaging by sending imaging signals from within the capsule to the imaging sensor that is located outside capsule 110 and distal to handle portion 102.

FIG. 2B shows a tip of device 100, according to an alternate embodiment of the present invention, where an optical fiber 111 is used for imaging. In this embodiment, optical fiber 111, during an operational state of device 100, conveys the image signals captured to an image sensor located outside and proximal to shaft 104 of device 100. As standard off the shelf optical fibers may be found having outer diameters of less than 0.5 mm, the diameter of capsule 110 of this embodiment may be reduced as it does not contain the sensor. As a result, the tip of this embodiment is more easily navigated through the narrow and tortuous path of the fallopian tubes and using optical fiber 111 represents an alternative embodiment of the present invention.

FIG. 3 shows a portion of device 200 (which is the operational state of device 100), according to one embodiment of the present invention. Device 200 includes a flexible wire 218, a fallopian tube-access device 228, a shaft portion 204, a seal-creating portion 206, an imaging subassembly 208 and capsule 210. Wire 218, shaft portion 204, seal-creating portion 206, imaging subassembly 208 and capsule 210 are substantially similar to their counterparts (i.e., wire 118, shaft portion 104, seal-creating portion 106, imaging subassembly 108 and capsule 110) shown in FIG. 1, except device 200 shows imaging subassembly 208 and capsule 210 being hydraulically propelled during an operational state of device 200. In one preferred embodiment of the present invention, device 200 includes a sail, which surrounds imaging subassembly 208, such that when the imaging subassembly is hydraulically propelled, the sails expand to enhance the hydraulic propulsion of the imaging subassembly.

Although in connection with FIGS. 2, 2A, 2B and 3, hydraulic propulsion is described to propel imaging subassembly 108, imaging optical fiber 111 or capsule 110, other preferred embodiments of the present invention contemplate hydraulically propelling therapy into the narrow body lumen. In this embodiment, imaging subassembly 108, imaging optical fiber 111 or capsule 110 are absent and electrical access port 114 is replaced by a therapy port. Furthermore, the therapy port is communicatively coupled to a therapy lumen, which replaces the wire lumen. Effective therapies contemplated by the present invention are detailed below. In another embodiment of the present invention, an electrical and therapeutic port co-exist to allow direct visualization as the therapy is being administered.

To effectively maintain fallopian tubes, the present invention also offers non-hydraulically propelled imaging or therapeutic devices. In certain embodiments of the present invention, a guidewire and/or a catheter, which is positioned over the guidewire, facilitate imaging or therapy. In other embodiments, the guidewire lumen of the present invention facilitates therapeutic intervention.

Figure 4A:
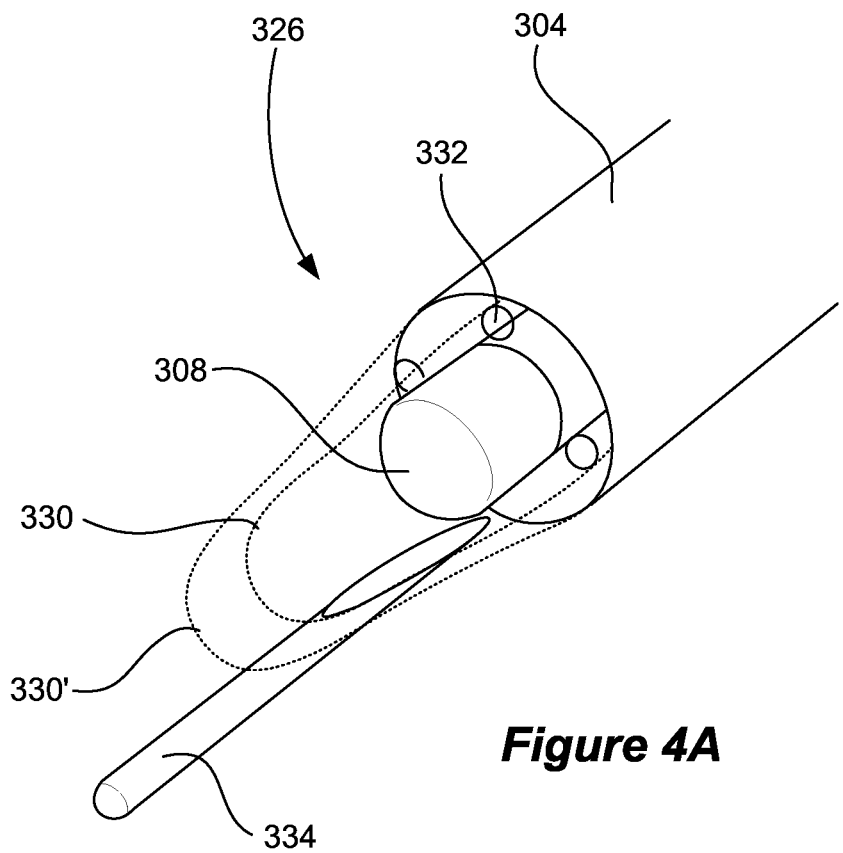
FIG. 4A is a perspective view of two different ovular-shaped distal tips, according to certain embodiments of the present invention, used in a guidewire-based diagnostic imaging device or in a guidewire lumen-based therapeutic intervention device.
Figure 4B:
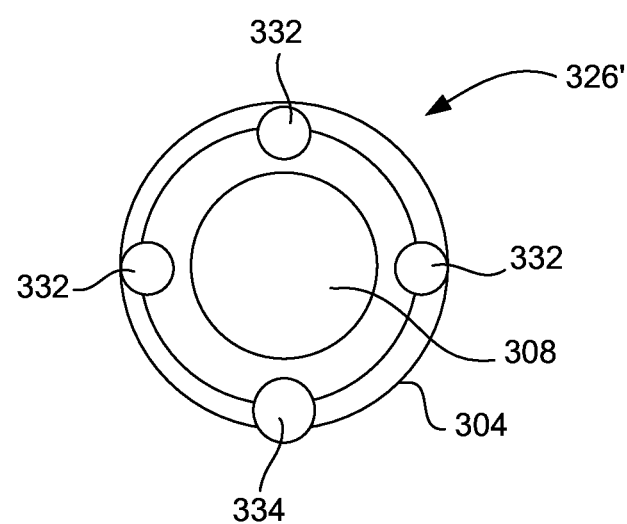
FIG. 4B is a top view of the distal tip shown in FIG. 4A.

FIG. 4A shows two different ovular-shaped protective shields, according to certain embodiments of the present invention, shown as part of a single distal tip 326, which may be designed to function either as a guidewire-based diagnostic imaging device or as a guidewire lumen-based therapeutic intervention device. FIG. 4B shows a top view of distal tip 326', which is the same as distal tip 326, except in a different orientation. Two different protective shields, i.e., a first protective shield 330 and a second protective shield 330', are shown in FIG. 4A as being part of single distal tip 326, those skilled in the art will recognize that only one protective shield is necessary in this embodiment of the present invention.

As shown in FIG. 4A, distal tip 326 of inventive catheters includes a shaft portion 304, one or more light sources 332, an imaging portion 308 and a guidewire 334. Guidewire 334 guide inventive catheters during an imaging procedure inside the fallopian tubes, for example. According to the present invention, however, guidewire 334 is preferably designed to provide light or is capable of sensing an image. To this end, guidewire 334 may contain illuminating fibers or imaging fibers. If an inventive catheter contains illuminating fibers, then the associated guide wire, which guides that catheter during operation, may include imaging fibers. Alternately, if the inventive catheter contains imaging fibers, then the associated guidewire 334 may include illuminating fibers. According to the present invention, in this manner, structures for carrying out illuminating and imaging functions may be distributed between a catheter and its associated guidewire. Separating a light source from an imaging sensor allows a device user to control the amount and angle of light needed to capture a clearer image (akin to a professional photographer having an external flash).

In certain embodiments of the present invention, guidewire 334 includes optical fibers for providing light to facilitate imaging, and may be made from fiber optics.

In accordance with one embodiment of the present invention, during an operation state of device with distal tip 326, guidewire 334 extends from a location outside the fallopian tube to another location inside the fallopian, such that light is conveyed from the location outside the fallopian tube to the location inside the fallopian tube. Having the source of the lighting remain outside of the fallopian tube will reduce heat exposure to the fallopian tubes.

In preferred embodiments of the inventive catheters, guidewire 334 includes a plurality of substantially transparent portions along a length of the guidewire. Each of the plurality of substantially transparent portions allow light to pass through. During an operational state of the catheter, each of the substantially transparent portions illuminate a plurality of different locations along the length of the fallopian tube that are adjacent to the substantially transparent portions. In this embodiment, a light emitting diode ("LED") may be located at or around a guidewire's tip and, as a result, incident light emanating from the LED exits from the substantially transparent portions and illuminates the tissue.

Inventive catheters may further include an image sensor located at a proximal end of a catheter shaft (e.g., 104 of FIG. 2) or inside a handle portion (e.g., 102 of FIG. 2) of the catheter. In this configuration of the inventive catheters, the above-mentioned imaging fibers extend along a length of the catheter shaft such that, during an operational state of the catheter, the imaging fibers facilitate imaging by sending imaging signals from a distal end of the catheter to the imaging sensor. Keeping the sensor outside of the catheter's shaft reduces an outer diameter of the catheter, and therefore, allows the physician to more easily navigate the fallopian tubes and reduces the potential for tissue trauma.

In alternate embodiments of the present invention, the catheters further include an image sensor for sensing an image. In this embodiment, the image sensor is located at a distal end of a catheter shaft such that, during an operational of the catheter, an image of the fallopian tube sensed by the imaging sensor is conveyed by the imaging fibers or by electrical wires, which extend along a length of the catheter shaft, to a display unit that is located outside the fallopian tube. Although this configuration may increase the catheter's outer diameter, it provides a clearer image as the sensor is located closer to the image being taken.

Protective shield 330 or 330' of FIG. 4A, during an operational state of the device, preferably protect an image sensor and/or imaging fibers and further provide an approximate focal length (that is associated with the image sensor) between the image sensor and/or the imaging fibers and the fallopian tube to obtain a substantially focused image. Protective shield of the present invention overcomes the drawback of the fallopian tube hanging over the catheter's tip, which makes it hard to capture a clear image.

In other preferred embodiments, inventive catheters include a light source (e.g., light source 332 shown in FIG. 4A) that is located at a distal end of a catheter shaft such that a substantially transparent protective shield (e.g., protective shield 330 or 330' of FIG. 4A) protects the image sensor and/or the imaging fibers, and the light source is located outside the protective shield as shown in FIG. 4A. This embodiment prevents illumination of the fallopian tube to be distorted by the presence of the substantially transparent protective shield.

The present invention recognizes that during an imaging operation, fallopian tube tissue might fold over a light source and block illumination, and thereby, prevent proper illumination of a target location. In alternate preferred embodiments, inventive catheters include a light source that is protected by the substantially transparent protective shield. In this embodiment, the presence of a protective shield, prevents the fallopian tube tissue from folding over and blocking the light source.

To reduce the risk of perforating the fallopian tube during an imaging operation as encountered by certain imaging attempts discussed above, inventive catheters preferably include a pressure sensor. In one implementation of this embodiment, the pressure sensor is located at a distal end of the guidewire and/or the catheter. During an imaging operation, the pressure sensor is capable of measuring a value of pressure exerted by the guidewire and/or the catheter against the fallopian tube. The pressure sensor may be communicatively coupled to a processor that provides an alert signal during an imaging operation. If, during an imaging operation, the value of pressure exerted by the guidewire and/or the catheter inside the fallopian tube is equal to or exceeds a predetermined unacceptable value of pressure, the pressure may provide the alert signal to a catheter's user (e.g., activating a red warning light on the handle).

Inventive catheters may further include a guidewire lumen having defined therein a channel for the guidewire (e.g., guidewire 334 of FIG. 4A). During an operational state of the catheter, and in absence of the guidewire inside the guidewire lumen (e.g., when an imaging operation has concluded), the channel inside the guidewire lumen is capable of transporting therapy to the fallopian tube.

The therapy includes at least one member selected from a group consisting of an anti-inflammatory agent, bio-absorbable stent and a drug-coated inflatable body. In certain embodiments of the present invention, a liquid anti-inflammatory agent is delivered locally to a diseased site. Inflammation (likely caused by infection) is thought to be the leading cause of fallopian tube occlusion.

In those embodiments of the present invention where therapy includes a bio-absorbable stent, the stent provides to the fallopian tubes both mechanical support and a drug, which treats a local disease and prevents the occlusion from recurring. After the stent is absorbed by the body and the disease is treated, the egg, may uninterruptedly pass from the ovaries through the fallopian tube to the uterus.

With respect to the drug-coated inflatable body, during an operational state of the catheter, when the inflatable body (such as a balloon) is expanded, debris found within the fallopian tube may be dislodged by the force it takes to expand the balloon. Furthermore, the inflatable body may be positioned within a partial blockage. In this case, the expansion force will applies sufficient mechanical force to a blockage and serves to clear the blockage.

Furthermore, the drug-coating on the inflatable body (e.g., anti-inflammatory agent) prevents recurrence of those blockages for a time adequate to allow for conception. On the other hand, drug coated balloons used to treat coronary artery disease, face the challenge of a continuous blood flow which eventually rids the artery of the drug. Consequently, the patient only temporarily sees the benefit of the therapy, where treatment of coronary artery disease needs to last a lifespan of a patient. In contrast, the fallopian tubes are not inherently fluid filled. Therefore, the drug will last longer in the diseased region of the fallopian tube. Furthermore, the impact of the drug need only last for as long as it takes the patient to conceive (on average 0 to 12 months). If the drug dissipates and blockages do occur at some point after conception, those blockages do not cause any pain or discomfort to the patient.

Figure 5A:
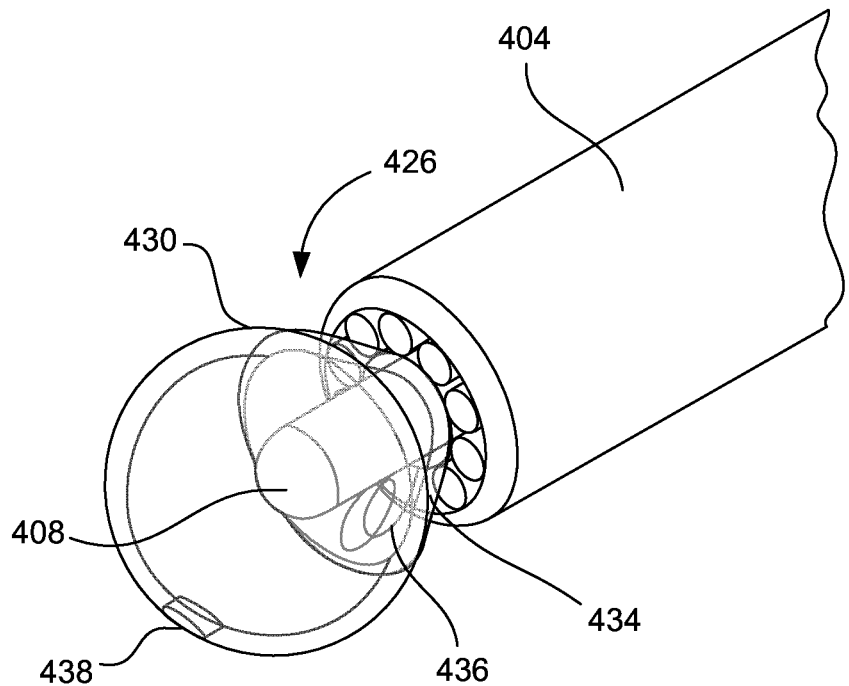
FIG. 5A is a perspective view of a conical-shaped distal tip, according to one embodiment of the present invention, used in a guidewire-based diagnostic imaging device or in a guidewire lumen-based therapeutic intervention device.

FIG. 5A shows a conical-shaped distal tip 426, according to one embodiment of the present invention. The conical-shaped distal tip 426 is preferably part of a guidewire-based diagnostic imaging device or in a guidewire lumen-based therapeutic intervention device. Regardless of the manner in which distal tip 426 is implemented, it includes a shaft portion 404, one or more light sources 432 (labeled in FIG. 5B), an imaging portion 408, a protective shield 430 and guidewire 434, all of which are substantially similar to their counterparts shown in FIG. 4A (i.e., shaft portion 304, one or more light sources 332, imaging portion 308, protective shield 330 and guidewire 334, respectively), except FIG. 5A shows an conical-shaped distal tip provides the image sensor a different focal length than that provided by the ovular-shaped distal tip of FIG. 4A, and protective shield 430 has defined therein an ingress aperture 436 and an egress aperture 438. During an imaging operation, guidewire 434, which is positioned outside protective shield 430, is capable of entering through ingress aperture 436 and exiting from egress aperture 438. In other words, apertures 436 and 438 allow guidewire 434 to pass through protective shield 430 and access a location in the fallopian tubes that is distal to protective shield 430. This will allow the physician to push away from the fallopian tube wall using the guidewire if additional distance is needed in order to capture a clear image.

Figure 5B:
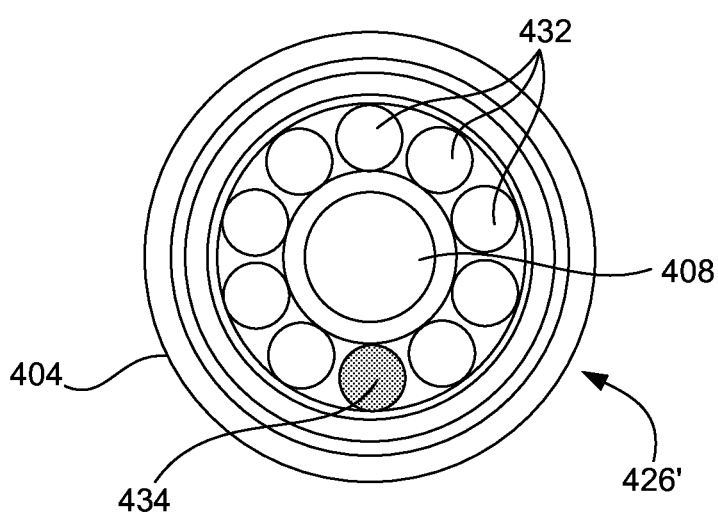
FIG. 5B is a top view of the distal tip shown in FIG. 5A.

Furthermore, the conical shape may introduce less tissue trauma than the ovular-shaped protective shield. FIG. 5B is a top view of a distal tip 426', which is the same as distal tip 426 shown in FIG. 5A, except distal tip 426' has a different orientation than distal tip 426.

Preferred embodiments of the present invention also provide non-guidewire based diagnostic imaging device or a non-guidewire lumen-based therapeutic intervention device. A non-guidewire based diagnostic imaging device includes a sensing lumen, a solution lumen and optionally a therapeutic lumen. The sensing lumen, in turn, includes a sensing portion and an inflatable portion. The sensing portion is capable of sensing information (e.g., imaging information) about the fallopian tube.

The solution lumen is designed to provide a solution, which facilitates sensing carried out by the sensing portion. The solution is also designed to flush the fallopian tube, ridding it of residual blood and mucous, which obscures the image. Furthermore, presence of the solution facilitates in the expansion of the fallopian tube and thereby reduces the chance of causing a perforation. Finally, therapeutic solutions used in the therapeutic are discussed above in greater detail.

During an operational state of the non-guidewire based diagnostic device, the inflatable portion inflates to create a space around the sensing portion such that in presence of the solution, the sensing portion senses information regarding the fallopian tube, including but not limited to the presence of sterilization implants and naturally occurring blockages. This space allows for there to be an adequate focal length between the sensing portion and the fallopian tube wall to facilitate capturing a clear image (e.g., a clear image may be taken if the sensing portion is a standard optical camera or light-wave scattering optical system). However, if the sensing portion consists of a sound-wave imaging system, then the inflatable portion creates a seal so that the fallopian tube may be filled with a liquid medium, through which sound waves can propagate.

The sensing portion may include at least one member selected from a group consisting of light source, a camera, an acoustic imaging system and a scattered-light imaging system. Certain current techniques used for cardiovascular imaging (e.g., intravascular ultrasound ("IVUS") and optical coherence tomography ("OCT")) utilize light scattering and acoustic imaging techniques, but do not lend themselves to imaging fallopian tubes because of their rigidity. Furthermore, current cardiovascular IVUS catheters are not capable of creating a seal to facilitate imaging of a structure which is inherently non-fluid filled because in the absence of a medium, sound waves do not travel. It is noteworthy that because the fallopian tube is non-fluid filled, a seal must be created and the fallopian tube must be filled with a liquid medium, such as saline, before imaging using sound waves can occur. Further still, these catheters have relatively large dimensions which make it difficult to access the length of the narrow and tortuous fallopian tube.

To this end, the present invention proposes that catheter designs of IVUS and OCT may be modified in a manner consistent with the different relevant inventive catheters. Inventive catheters described herein are not limited to IVUS and OCT applications, and work well with other optical imaging techniques (e.g., imaging carried out by complementary metal oxide semiconductor ("CMOS") or optical fiber). In accordance with preferred embodiments, inventive catheters include unique atraumatic tips and/or inflatable bodies as described below.

The imaging information collected by image portion 508 provides such information about the fallopian tube as naturally occurring blockage, inflammation, hydrosalpinx, sterilization implants operatively placed in the fallopian tubes and disease of the fallopian tube. This information is particularly valuable in diagnosing fallopian tube disorder and allows for disease-specific therapeutic intervention, if needed.

Figure 6A:
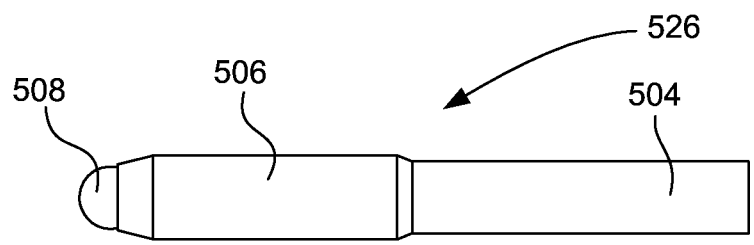
FIG. 6A is a side view of a non-inflated conical-shaped distal tip, according to one embodiment of the present invention, used in a non-guidewire-based diagnostic imaging device or in a non-guidewire lumen-based therapeutic intervention device.

FIG. 6A shows a non-guidewire based diagnostic device where the sensing portion senses image information about the fallopian tube, allowing the physician to diagnose disease. Specifically, FIG. 6A is a side view of a non-inflated conical-shaped distal tip 526, according to one embodiment of the present invention that is preferably used in a non-guidewire-based diagnostic imaging device or in a non-guidewire lumen-based therapeutic intervention device. Distal tip 526 includes an imaging portion 508, an inflatable portion 506 and a shaft portion 504. Imaging portion 508 and shaft portion 504 are substantially similar to their counterparts in FIG. 5A (i.e., imaging portion 408 and shaft portion 404), except shaft portion 404 of FIG. 5A contains a guidewire 434.

In accordance with one preferred embodiment, inventive distal tips include a pressure sensor located at a distal end of a catheter and are designed to measure a value of pressure exerted by the catheter during an operational state of the device. The pressure sensor features described above to alert a user of undue excessive pressure may also be incorporated in this embodiment.

Figure 6B:
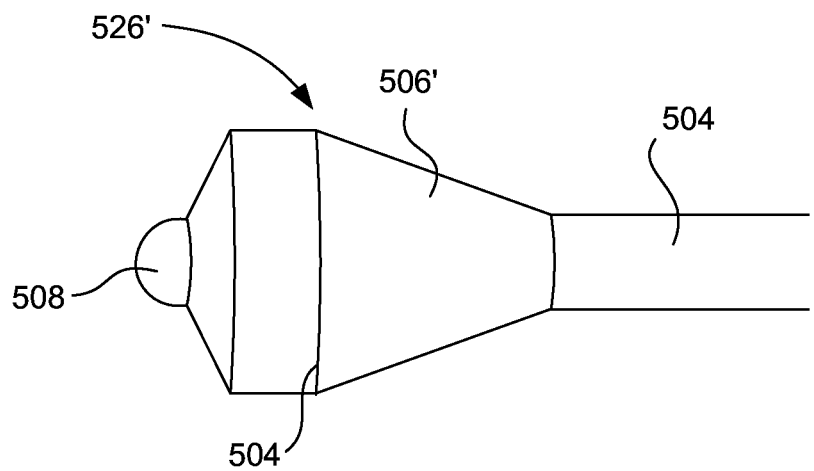
FIG. 6B is a side view of the conical-shaped distal tip of FIG. 6A in its inflated state.

FIG. 6B is a side view of the conical-shaped distal tip of FIG. 6A in its inflated state. Inflatable portion 506, in its inflated state (i.e., inflated portion 506' of FIG. 6B) has an atraumatic shape, which is one shape selected from a group consisting of conical, ovular and dome.

Figure 7A:
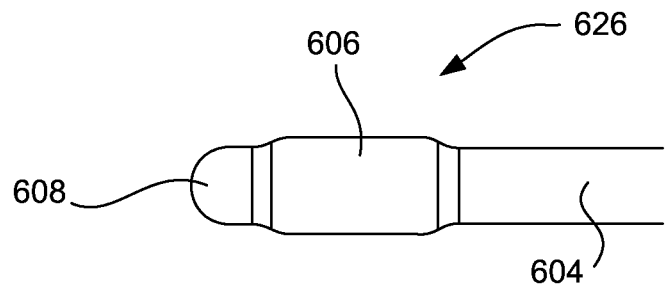
FIG. 7A is a side view of a non-inflated ovular-shaped distal tip, according to one embodiment of the present invention, used in a non-guidewire-based diagnostic imaging device or in a non-guidewire lumen-based therapeutic intervention device.
Figure 7B:
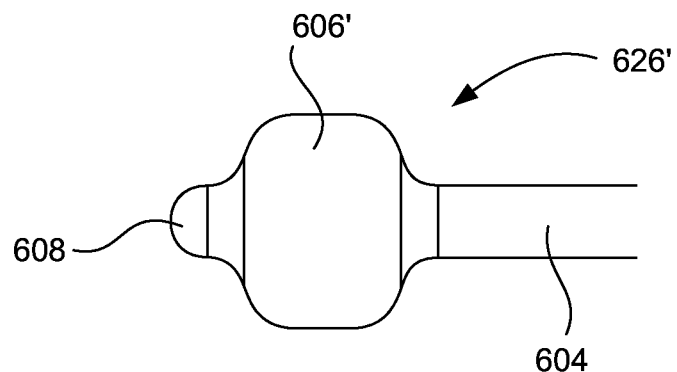
FIG. 7B is a side view of the ovular-shaped distal tip of FIG. 7A in its inflated state.

FIG. 7A is a side view of another non-inflated ovular-shaped distal tip 626, according to one embodiment of the present invention, also preferably used in a non-guidewire-based diagnostic imaging device or in a non-guidewire lumen-based therapeutic intervention device. Distal tip 626 is substantially similar to distal tip 526 of FIG. 6A (i.e., imaging portion 608 and shaft portion 604 are substantially similar to imaging portion 508 and shaft portion 504 of FIG. 6A), except inflatable portion 606 of FIG. 7A has a different shape than inflatable portion 506 of FIG. 6A. The differences in shape between inflatable portions 506 and 606 are evident in their respective inflated states and may correspond to different focal lengths and different amounts of tissue trauma. FIG. 7B is a side view of ovular-shaped distal tip 626', which is in an inflated state of distal tip 626 of FIG. 7A.

Figure 8A:
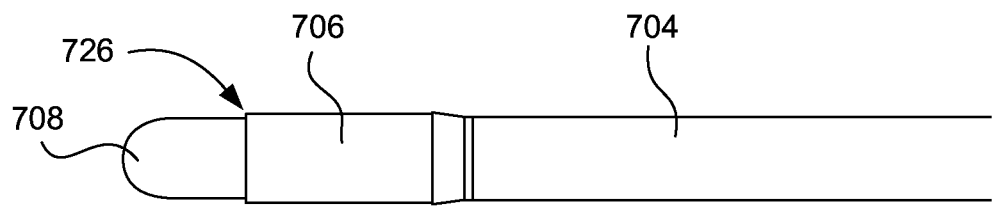
FIG. 8A is a side view of a non-inflated dome-shaped distal tip, according to one embodiment of the present invention, used in a non-guidewire-based diagnostic imaging device or in a non-guidewire lumen-based therapeutic intervention device.
Figure 8B:
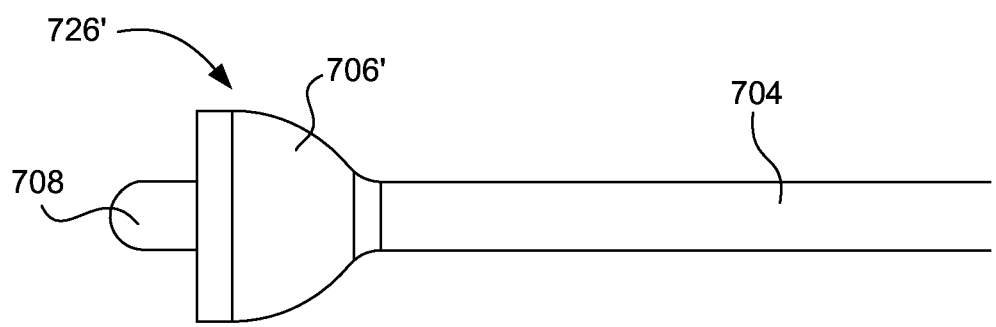
FIG. 8B is a side view of the dome-shaped distal tip of FIG. 8A in its inflated state.

FIG. 8A is a side view of a non-inflated dome-shaped distal tip 726, according to one embodiment of the present invention, preferably used in a non-guidewire-based diagnostic imaging device or in a non-guidewire lumen-based therapeutic intervention device. Distal tip 726 is substantially similar to distal tip 526 of FIG. 6A (i.e., imaging portion 708 and shaft portion 704 are substantially similar to imaging portion 508 and shaft portion 504 of FIG. 6A), except inflatable portion 706 of FIG. 8A has a different shape than inflatable portion 806 of FIG. 6A. Like the differences between inflatable portions 506 and 606, the differences in shape among inflatable portions 506, 606 and 706 are evident in their respective inflatable states. FIG. 8B is a side view of ovular-shaped distal tip 726', which is in an inflated state of distal tip 726 of FIG. 7A.

Figure 8C:
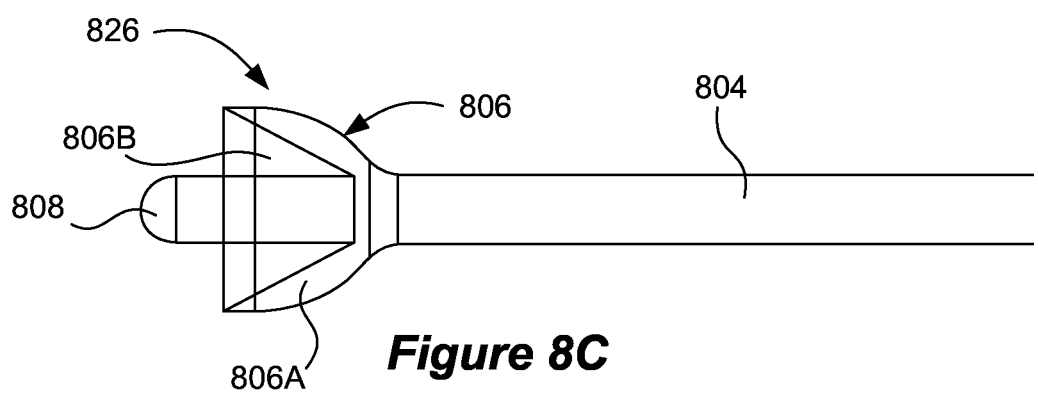
FIG. 8C shows certain major components, according to one embodiment of the present invention, in the distal tip as shown in FIG. 8B.

FIG. 8C shows certain major components, according to one embodiment of the present invention, in an inflated distal tip 826, which is substantially similar to inflated distal tip 726' of FIG. 8B. FIG. 8C shows a more detailed structure that is preferably contained within inflatable portion 806. According to this figure, inflatable portion 806 includes an inflatable component 806A and a non-inflatable component 806B. During an operational state of the device, the inflatable component 806A inflates, while non-inflatable component 806B does not inflate, but serves to provide mechanical support to inflatable portion 806.

Figure 9:
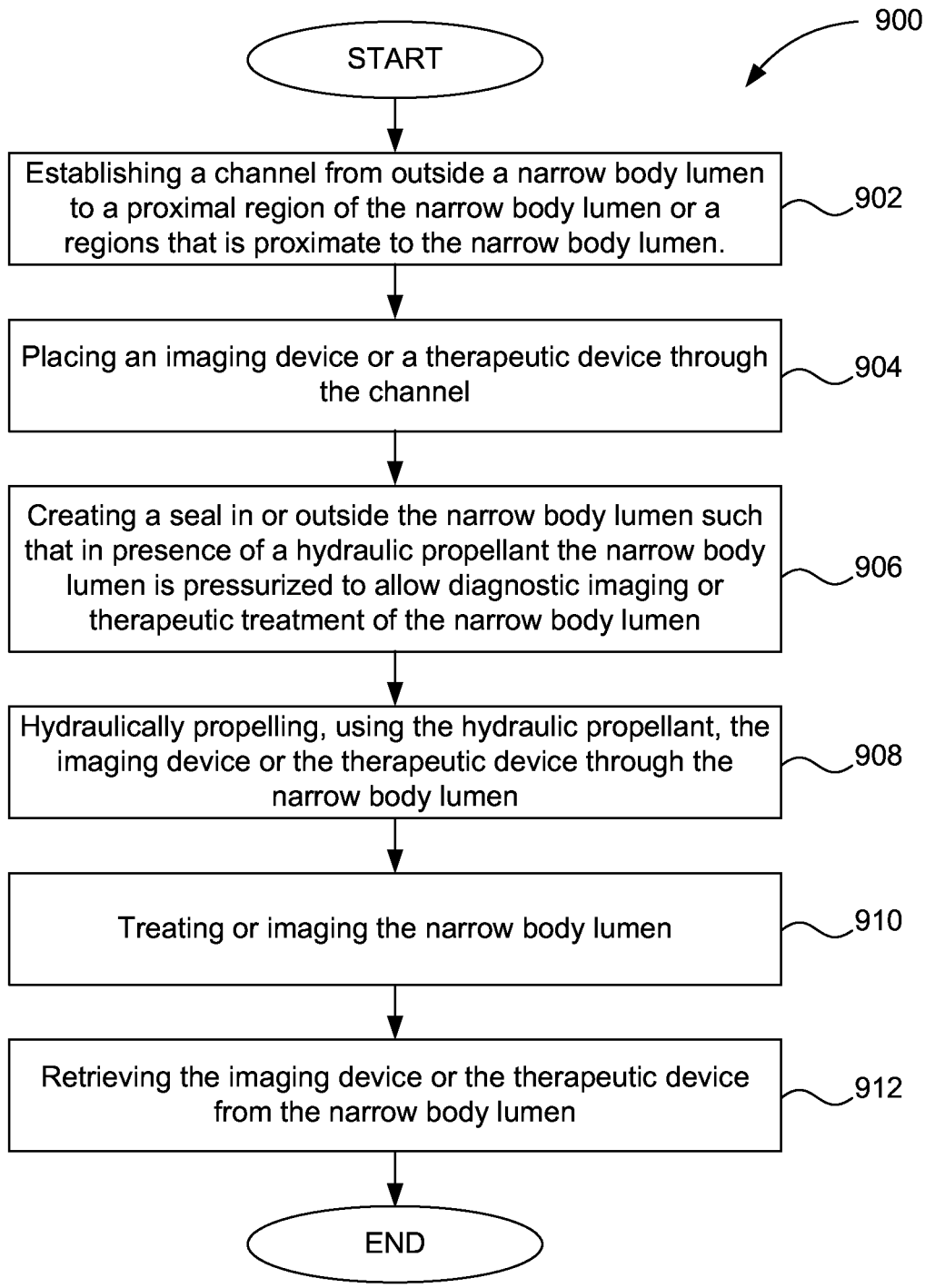
FIG. 9 shows a process flow diagram, according to one embodiment of the present invention that uses a hydraulic propulsion mechanism for diagnostic imaging.

FIG. 9 shows a process flow diagram 900, according to one embodiment of the present invention that uses a hydraulic propulsion mechanism for diagnostic imaging. Preferably process 900 begins in step 902, which involves establishing a channel from outside a narrow body lumen to a proximal region of the narrow body lumen or a region that is proximate to the narrow body lumen. By way of example, a hysteroscope is used to visualize and gain access to the ostia of the fallopian tubes within uterus. In this case, the working channel of the hysteroscope establishes the channel of step 902 from outside the fallopian tube to the ostia of the fallopian tube within uterus.

Next, step 904 of FIG. 9 includes placing an imaging device or a therapeutic device through the channel. Continuing with the above example of the hysteroscope, step 904 is carried out by introducing shaft portion 104 of device 100 of FIG. 2 through the working channel of the hysteroscope until the distal end of shaft portion 104 is slightly distal to the distal end of the hysteroscope's working channel or until the distal end of shaft portion 104 is located in the approximate region of the fallopian tube.

In this configuration, step 906 of FIG. 9 is carried out. Step 906 includes creating a seal in or outside the narrow body lumen such that in presence of a hydraulic propellant the narrow body lumen is pressurized to allow diagnostic imaging or therapeutic treatment of the narrow body lumen. In order to create a seal in the fallopian tube, for example, the seal-creating portion 106 of FIG. 2 may be expanded either proximal to the fallopian tube ostia in the uterus or within the proximal region of the fallopian tube. The seal will allow pressure to build the portion of the device which is meant to be hydraulically propelled.

Then, another step 908 of FIG. 9 includes hydraulically propelling, using the hydraulic propellant, the imaging portion (108 of FIG. 2A) or the therapeutic device contained in the capsule (110 of FIG. 2A) through the narrow body lumen. By way of example, device 200 of FIG. 3 shows a capsule 210, which is attached to handle portion 102 of FIG. 2 by a wire 218 of FIG. 3, being hydraulically propelled. Several steps may be taken to aid in the propulsion of the capsule (e.g., capsule 210 of FIG. 3). The capsule, which may be made from a substantially transparent material, is preferably inflated. Alternately, the capsule may contain an inflatable body, such as a balloon, which is preferably inflated. These steps enhance the buoyancy of the capsule, aiding the propulsion of the capsule. Furthermore, in its propelled state, sails 238 of FIG. 3 attached to imaging subassembly 208 will deploy to capture the hydraulic propellant (which is akin to sails on a sail boat that capture the power of wind to propel the boat's forward movement).

After step 908 and once a diseased portion of the fallopian tube or the fimbria of the fallopian tube is reached, step 910 of FIG. 9 includes treating or imaging the narrow body lumen. As discussed above in reference to FIGS. 2, 2A, 2B and 3 imaging is carried out by imaging subassembly 108 of FIG. 2A. Imaging, according to certain embodiments of inventive step 908, is carried out in an antegrade fashion (during forward propulsion of imaging subassembly 108) or retrograde fashion (during retrieval of imaging subassembly 108). With respect to treating the narrow body lumen, once the disease state is imaged, one therapy selected from a group consisting of flushing saline to rid the fallopian tube of debris, applying anti-inflammatory agent in liquid form and applying mechanical force to an occlusion using an inflatable body (e.g., seal-creating portion 104 of FIG. 2), is preferably carried out.

Process 900 preferably comes to an end in step 912 of FIG. 9, which involves retrieving the imaging device from the narrow body lumen. By way of example, retrieval mechanism 122 of FIG. 2 is activated to retrieve the imaging device from the fallopian tube. The retrieval mechanism is preferably activated by engaging a reel mechanism (e.g., mechanism 122 of FIG. 2), which is placed on the handle. Alternately, the entire device may be pulled back towards the user to remove it from the narrow body lumen.

It is noteworthy that steps 902 and 904 of FIG. 9 are optional and that the steps mentioned above need not be carried out in any particular order. Rather the sequence of steps described above represent a more preferred embodiment of the present invention. Process 900 can be carried out using any structure and is not limited to any structure shown in FIGS. 2, 2A, 2B and 3. The structures shown in these figures serve as examples and are used to facilitate discussion regarding process 900.

Figure 10:
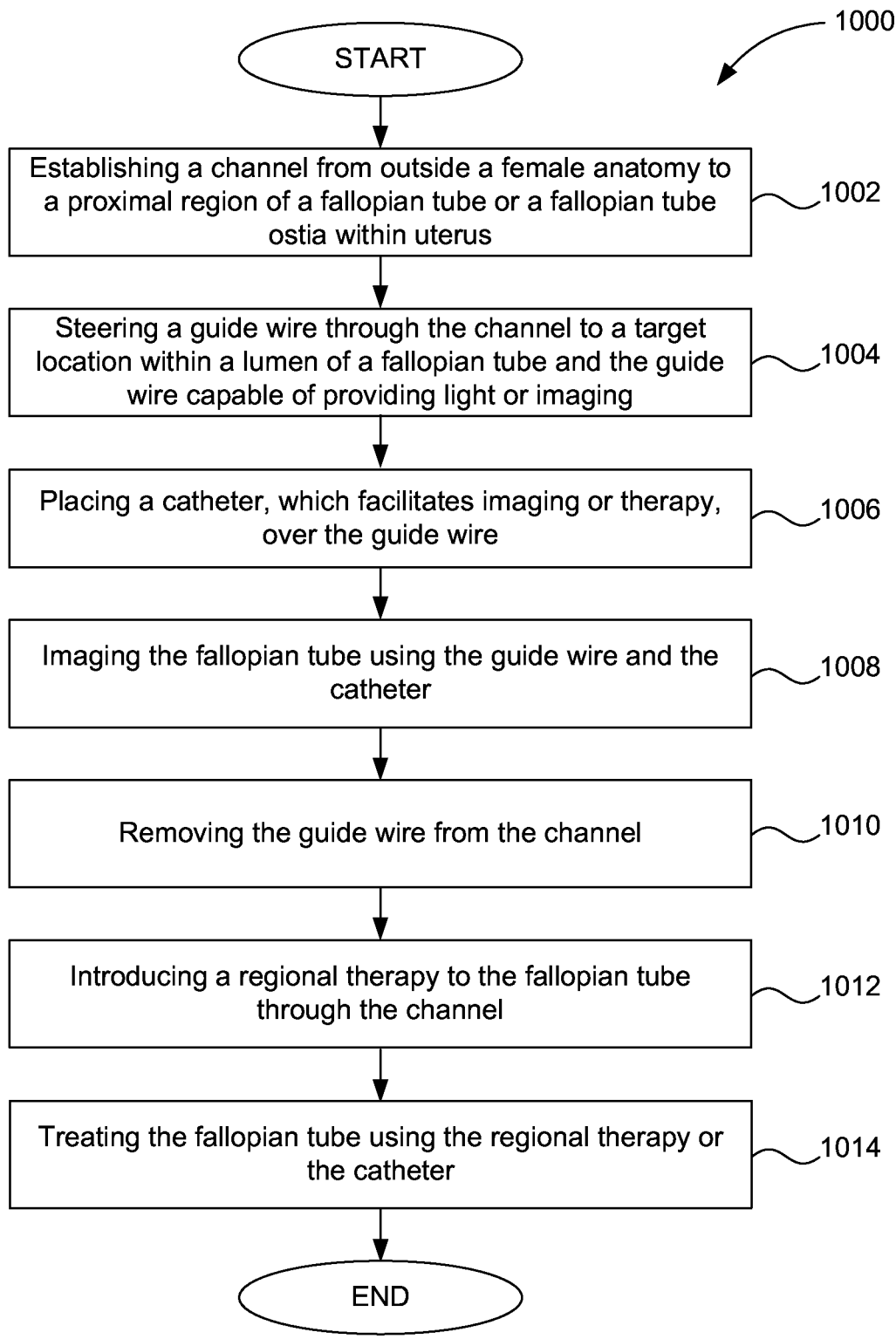
FIG. 10 shows a process flow diagram, according to one embodiment of the present invention that uses a guide wire mechanism for diagnostic imaging.

FIG. 10 shows a process flow diagram 1000, according to one embodiment of the present invention that uses a guidewire mechanism for diagnostic imaging. Preferably process 1000 begins in step 1002, which involves establishing a channel from outside a female anatomy to a proximal region of a fallopian tube or a fallopian tube ostia within uterus. Step 1002 is substantially similar to the imaging aspect of step 902 of FIG. 9.

Next, step 1004 includes steering a guidewire through the channel to a target location within a lumen of a fallopian tube and the guidewire capable of providing light or imaging. By way of example, guidewire 334 in FIG. 4A is bundle of optical fiber capable of providing light or imaging a fallopian tube.

In this configuration, step 1006 is carried out. Step 1006 includes placing a catheter, which facilitates imaging or therapy, over the guide wire. Depending on whether guidewire 334 of FIG. 4A is capable of imaging or illuminating, the catheter contains the complementary structure to facilitate imaging.

Then, another step 1008 includes imaging the fallopian tube using the guidewire and the catheter. By way of example, imaging as required by this step is carried out by positioning guidewire 334 of FIG. 4A relative to the catheter (e.g., catheter 304 of FIG. 4A) so that the correct amount and angle of light illuminates the portion of fallopian tube being imaged. Furthermore, a protective shield (e.g., shield 330 of FIG. 4A) is positioned so that the appropriate focal length is achieved between the fallopian tube wall and the imaging portion (e.g., imaging portion 308 of FIG. 4A).

After step 1008, step 1010 includes removing the guidewire from the channel. Continuing with the guidewire example of FIG. 4A, guidewire 344 is removed from the hysteroscope's working channel referenced in step 1002 of FIG. 10. This allows the guidewire channel to be used for delivery of therapy.

Next step 1012 includes introducing regional therapy to the fallopian tube through the channel. Therapy in this step is preferably introduced by way of an additional therapeutic catheter or in liquid form through the guidewire channel discussed above.

Process 1000 preferably comes to an end in step 1014, which involves treating the fallopian tube using the regional therapy or the catheter. Therapy in this step is preferably one therapeutic solution selected from a group consisting of applying an anti-inflammatory agent in liquid form, introducing a drug-coated balloon (e.g., coated with an anti-inflammatory), introducing a bio-absorbable stent and flushing with saline to remove debris from the fallopian tube.

It is noteworthy that steps 1002, 1010, 1012 and 1014 are optional and that the steps mentioned above need not be carried out in any particular order. Rather the sequence of steps described above represent a more preferred embodiment of the present invention. In one preferred embodiment of the present invention, another step may be added. Specifically, after imaging has concluded at the end of step 1008, another step, which includes retrieving the catheter from the fallopian tube is more preferably carried out. Process 900 can be carried out using any structure and is not limited to any structure shown in FIGS. 4A, 4B, 5A and 5B. The structures shown in these figures serve as examples and are used to facilitate discussion regarding process 1000.

Although illustrative embodiments of this invention have been shown and described, other modifications, changes, and substitutions are intended. By way of example, the present invention discloses fallopian tubes as an exemplar of a narrow body lumen, which may undergo maintenance, and other anatomical structures, such as coronary arteries, may be similarly maintained Accordingly, it is appropriate that the appended claims be construed broadly and in a manner consistent with the scope of the disclosure, as set forth in the following claims.

What is claimed is:

1. A device for maintaining a narrow body lumen, comprising:
a hydraulic propulsion mechanism and at least one of an imaging portion or a therapeutic portion, said hydraulic propulsion mechanism configured for propelling said imaging portion or said therapeutic portion relative to said hydraulic propulsion mechanism and through the narrow body lumen, said hydraulic propulsion mechanism including an elongate shaft, wherein the narrow body lumen is distal of a distal end of said elongated shaft;
wherein said imaging portion or said therapeutic portion, when propelled by said hydraulic propulsion mechanism, is driven distally from said distal end of said elongated shaft and is distally spaced therefrom; and
a retrieval mechanism for retrieving said imaging portion or said therapeutic portion from the narrow body lumen.

2. The device of claim 1, further comprising at least one luer configured to provide hydraulic pressure through said elongate shaft to hydraulically propel said imaging portion or said therapeutic portion through said narrow body lumen.

3. The device of claim 2, further comprising a wire luer configured to provide a wire for conveying electrical power and signals to facilitate an imaging function carried out by said imaging portion; and an inflation luer configured to inflate an inflatable body and create a seal to facilitate imaging and therapeutic treatment.

4. The device of claim 1, further comprising an inflatable body located outside of said shaft.

5. The device of claim 1, wherein said hydraulic propulsion mechanism includes:
  a luer designed receive a hydraulic propellant; and
  a hydraulic propellant lumen extending through at least a portion of said elongate shaft, said lumen being communicatively coupled to said luer and, using said hydraulic propellant, being capable of hydraulically propelling said imaging portion or said therapeutic portion.

6. The device of claim 1, wherein said imaging portion or said therapeutic portion, during an operational state of said device, forms a seal with the inner diameter of said shaft to allow for hydraulic propulsion of said imaging device or said therapeutic device.

7. The device of claim 1, further comprising a locking mechanism, which locks said imaging portion or said therapeutic portion relative to said shaft until a requisite pressure is achieved to enable hydraulic propulsion.

8. The device of claim 1, further comprising a sail which surrounds said imaging portion or said therapeutic portion such that when said imaging portion or said therapeutic portion is hydraulically propelled, said sail expands to enhance the hydraulic propulsion of said imaging portion or said therapeutic portion.

9. The device of claim 1, wherein said device comprises said imaging portion and said imaging portion includes at least one member selected from a group consisting of an image sensor and a light source; said imaging portion further including a capsule, wherein said capsule is made from a substantially transparent material, ensures a focal length from a subject being imaged by said imaging portion and encapsulates said at least one member.

10. The device of claim 9, wherein said image sensor includes at least one member selected from a group consisting of a charge coupled device (CCD), a complementary metal oxide semiconductor (CMOS) and an optical fiber.

11. The device of claim 9, wherein said capsule is substantially transparent to allow imaging of said narrow body lumen.

12. The device of claim 11, wherein said capsule is inflatable and contains said imaging portion, such that when said capsule is inflated, said imaging portion is positioned near or at an approximate focal length away from the narrow body lumen to allow focused imaging of the narrow body lumen, wherein said approximate focal length is associated with said imaging portion.

13. The device of claim 1, further comprising a capsule configured to encapsulate said imaging portion of therapeutic portion, said capsule comprising an inflatable body to enhance buoyancy of said imaging portion or said therapeutic portion and facilitate hydraulic propulsion of said imaging portion or said therapeutic portion.

14. The device of claim 1, further comprising a microgenerator which uses a hydraulic propellant to provide power for said imaging portion or said therapeutic portion, and wherein said microgenerator converts hydraulic energy into electrical energy.

15. The device of claim 1, further comprising a flexible wire communicatively coupled to said imaging portion or said therapeutic portion to facilitate propulsion of said imaging portion or said therapeutic portion through a tortuous pathway inside the narrow body lumen.

16. The device of claim 1, further comprising:
  a pressure sensor; and
  a pressure indicator;
  wherein said pressure sensor is designed to measure pressure being applied against said narrow body lumen and to convey a measurement of pressure to said pressure indicator, and if said measurement of pressure equals or exceeds a predetermined value of pressure, then said pressure indicator transmits an alert signal.

17. The device of claim 1, wherein said retrieval mechanism includes:
  a flexible wire communicatively coupled to said imaging portion or said therapeutic portion;
  a reel capable of reeling back said flexible wire from a propelled state; and
  wherein when said reel is activated, said imaging portion or said therapeutic portion is retrieved from a propelled state of said imaging portion or said therapeutic portion.

18. The device of claim 1, further comprising a pressure sensor, which senses pressure on said imaging portion or said therapeutic portion, as it is retrieved from said narrow body lumen.

19. The device of claim 1, wherein said imaging portion or said therapeutic portion contacts said distal end of said elongated shaft when in a non-propelled configuration; and
  wherein said imaging portion or therapeutic portion separates distally from said distal end of said elongate shaft when propelled by said hydraulic propulsion mechanism.

20. The device of claim 19 wherein said imaging portion or said therapeutic portion forms a seal with said distal end of said elongated shaft when in said non-propelled configuration; and
  wherein said imaging portion or therapeutic portion breaks said seal and separates distally from said distal end of said elongate shaft when propelled by said hydraulic propulsion mechanism.

21. A method of maintaining a narrow body lumen, said method comprising:
  sealing the narrow body lumen with a sealing member at a location to allow therapeutic treatment of said narrow body lumen using a therapeutic device;
  hydraulically propelling said therapeutic device distally of a main body and said location through said narrow body lumen;
  treating said narrow body lumen; and
  retrieving said therapeutic device from said narrow body lumen.

22. The method of claim 21, further comprising:
  defining a channel from outside said narrow body lumen to a proximal region of said narrow body lumen or a region that is proximate to said narrow body lumen; and
  placing said therapeutic device through said channel;
  wherein said placing is carried out before said sealing.

23. A method of maintaining a narrow body lumen, said method comprising:
  sealing the narrow body lumen with a sealing member at a location to allow imaging of said narrow body lumen using an imaging device;
  hydraulically propelling said imaging device distally of a main body and said location through said narrow body lumen;
  imaging said narrow body lumen; and
  retrieving said imaging device from said narrow body lumen.

24. A device for maintaining a narrow body lumen, comprising:
  a hydraulic propulsion mechanism and at least one of an imaging portion or a therapeutic portion, said hydraulic propulsion mechanism configured for propelling said imaging portion or said therapeutic portion through the narrow body lumen, said hydraulic propulsion mechanism including an elongate shaft;
a retrieval mechanism for retrieving said imaging portion or said therapeutic portion from the narrow body lumen; and
a microgenerator which uses a hydraulic propellant to provide power for said imaging portion or said therapeutic portion, and wherein said microgenerator converts hydraulic energy into electrical energy.

* * * * *